United States Patent
Duff

(10) Patent No.: US 9,898,584 B2
(45) Date of Patent: Feb. 20, 2018

(54) SYSTEM AND METHOD FOR PROVIDING A COMMON MEDICAL DEVICE ARCHITECTURE

(71) Applicant: Abbott Medical Optics Inc., Santa Ana, CA (US)

(72) Inventor: Richard G Duff, Irvine, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 412 days.

(21) Appl. No.: 13/841,270

(22) Filed: Mar. 15, 2013

(65) Prior Publication Data
US 2014/0278473 A1   Sep. 18, 2014

(51) Int. Cl.
G06F 13/10   (2006.01)
G06F 9/44   (2006.01)
G06F 19/00   (2011.01)

(52) U.S. Cl.
CPC ...... *G06F 19/3406* (2013.01); *G06F 19/3412* (2013.01)

(58) Field of Classification Search
None
See application file for complete search history.

(56) References Cited

U.S. PATENT DOCUMENTS

| | | | |
|---|---|---|---|
| 2004/0196039 A1* | 10/2004 | Haworth | G01R 33/28 324/318 |
| 2009/0240526 A1 | 9/2009 | Vesto et al. | |
| 2010/0121257 A1* | 5/2010 | King | A61M 1/0058 604/22 |
| 2011/0054936 A1 | 3/2011 | Cowan et al. | |
| 2013/0317753 A1* | 11/2013 | Kamen et al. | 702/19 |
| 2014/0188514 A1* | 7/2014 | Balignasay et al. | 705/3 |
| 2016/0095976 A1* | 4/2016 | Simpson | G06F 19/3418 604/66 |

OTHER PUBLICATIONS

International Search Report and Written Opinion for Application No. PCT/US2014/018543, dated Jul. 1, 2014, 12 pages.
Tody D, "Message Bus and Distributed Object Technology," in: Astronomical Data Analysis Software and Systems VII, A.S.P. Conference Series, 1998, Albrecht R., Eds., vol. 145, pp. 146-149.

* cited by examiner

*Primary Examiner* — Ilwoo Park
(74) *Attorney, Agent, or Firm* — Abbott Medical Optics Inc.

(57) ABSTRACT

Systems, methods, and computer readable storage medium for providing a genericized medical device architecture common to a plurality of medical devices are disclosed. The architecture may comprise at least one diagnostics module associated with at least one of the plurality of medical devices, wherein the at least one diagnostics module is configured to monitor an operational status of the at least one medical device. At least one hardware abstraction layer may be associated with at least one of the plurality of medical devices, and may be configured to provide abstracted access to hardware of the at least one medical device.

31 Claims, 10 Drawing Sheets

SYSTEM AND METHOD FOR PROVIDING A COMMON MEDICAL DEVICE ARCHITECTURE

CROSS-REFERENCE TO RELATED APPLICATIONS

This application is related to U.S. patent application Ser. No. 13/833,547, filed on Mar. 15, 2013, and entitled "SYSTEM AND METHOD FOR PROVIDING A USER INTERFACE TO REMOTELY CONTROL MEDICAL DEVICES", the entire disclosure of which is hereby incorporated by reference as if set forth herein in its entirety.

FIELD OF THE DISCLOSURE

The instant disclosure relates to device architectures, and in particular, to systems and methods for providing genericized medical device architectures.

BACKGROUND OF THE DISCLOSURE

In today's technologically driven world, the importance of innovation and product development is growing. Businesses must develop innovative products faster and more efficiently. This speed-to-market is achieved by maximizing effectiveness in both the product design and manufacturing stages of a product development cycle.

However, the perfection, or, at least the improvement of these stages may be stifled due to the heterogeneous hardware and/or software needs of any particular product or types of products developed by a business. Further, it goes without saying that lengthy product development cycles may have devastating effects on a business's bottom line. For example, one company may engage in the business of developing and producing several different types of medical devices, each with their own set of varying hardware and software configurations.

Despite the diversity that may exist among a family of medical device products, a lot of functionality may still be identified as common to the product family. For example, much of the software and/or hardware components in many medical devices may be common to a given family of devices produced by a given business. By exploiting these commonalities, development of several different products of a given product family may be performed in parallel. Consequently, a product(s) development cycle may be accelerated.

Therefore, there is a need for genericized medical device software architecture reflecting these commonalities, to be used in multiple products' development cycle. The architecture may allow for the changing needs of a business and its products, while still supporting a quick development cycle. Once a product using this software architecture is fielded, it may easily be extended and maintained without the creation of a whole new product.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts.

SUMMARY OF THE DISCLOSURE

The present disclosure includes systems, methods, and computer readable storage medium for providing a genericized medical device architecture common to a plurality of medical devices. The architecture may interact with and/or control a series of modules, such as a location independent communications module configured to provide message bus services for the series of modules. The architecture may also include a diagnostics module associated with one of the plurality of medical devices, wherein the diagnostics module is configured to monitor an operational status of the at least one medical device. A hardware abstraction layer may also be associated with one of the plurality of medical devices, and may be configured to provide abstracted access to hardware of the at least one medical device.

DETAILED DESCRIPTION OF THE EMBODIMENTS

It is to be understood that the figures and descriptions of the present disclosure have been simplified to illustrate elements that are relevant for a clear understanding of the present invention, while eliminating, for the purposes of clarity and brevity, many other elements found in typical software architectures. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Figure 1:
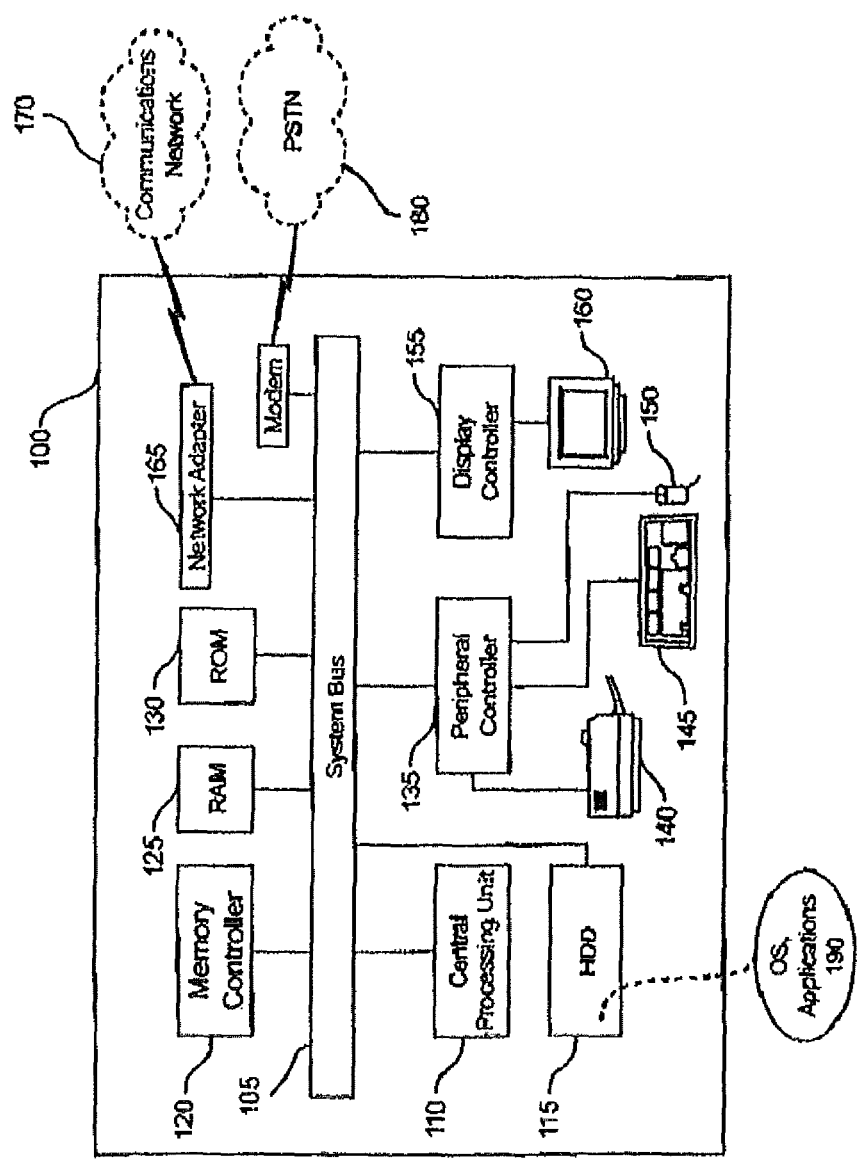
FIG. 1 illustrates a diagram of an exemplary computing system according to embodiments of the present invention.

FIG. 1 depicts an exemplary computing system 100 for use in accordance with herein described system and methods. Computing system 100 is capable of executing software, such as an operating system (OS) and a variety of computing applications 190. The operation of exemplary computing system 100 is controlled primarily by computer readable instructions, such as instructions stored in a computer readable storage medium, such as hard disk drive (HDD) 115, optical disk (not shown) such as a CD or DVD, solid state drive (not shown) such as a USB "thumb drive," or the like. Such instructions may be executed within central processing unit (CPU) 110 to cause computing system 100 to perform operations. In many known computer servers, workstations, personal computers, and the like, CPU 110 is implemented in an integrated circuit called a processor.

It is appreciated that, although exemplary computing system 100 is shown to comprise a single CPU 110, such description is merely illustrative, as computing system 100 may comprise a plurality of CPUs 110. Additionally, computing system 100 may exploit the resources of remote CPUs (not shown), for example, through communications network 170 or some other data communications means.

In operation, CPU 110 fetches, decodes, and executes instructions from a computer readable storage medium such as HDD 115. Such instructions may be included in software such as an operating system (OS), executable programs such as the aforementioned "apps", and the like. Information, such as computer instructions and other computer readable data, is transferred between components of computing system 100 via the system's main data-transfer path. The main data-transfer path may use a system bus architecture 105, although other computer architectures (not shown) can be used, such as architectures using serializers and deserializers and crossbar switches to communicate data between devices over serial communication paths. System bus 105 may include data lines for sending data, address lines for sending addresses, and control lines for sending interrupts and for operating the system bus. Some busses provide bus arbitration that regulates access to the bus by extension cards, controllers, and CPU 110. Devices that attach to the busses and arbitrate access to the bus are called bus masters. Bus master support also allows multiprocessor configurations of the busses to be created by the addition of bus master adapters containing processors and support chips.

Memory devices coupled to system bus 105 may include random access memory (RAM) 125 and/or read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode may normally access only memory mapped by its own process virtual address space; in such instances, the program cannot access memory within another process' virtual address space unless memory sharing between the processes has been set up.

In addition, computing system 100 may contain peripheral controller 135 responsible for communicating instructions using a peripheral bus from CPU 110 to peripherals, such as printer 140, keyboard 145, and mouse 150. An example of a peripheral bus is the Peripheral Component Interconnect (PCI) bus.

Display 160, which is controlled by display controller 155, may be used to display visual output and/or presentation generated by or at the request of computing system 100, responsive to operation of the aforementioned computing program, such as an app. Such visual output may include text, graphics, animated graphics, and/or video, for example. Display 160 may be implemented with a CRT-based video display, an LCD or LED-based display, a gas plasma-based flat-panel display, a touch-panel display, or the like. Display controller 155 includes electronic components required to generate a video signal that is sent to display 160.

Further, computing system 100 may contain network adapter 165 which may be used to couple computing system 100 to external communication network 170, which may include or provide access to the Internet, an intranet, an extranet, or the like. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

Network adaptor 165 may communicate to and from network 170 using any available wired or wireless technologies. Such technologies may include, by way of non-limiting example, cellular, Wi-Fi, Bluetooth, infrared, or the like.

It is appreciated that exemplary computing system 100 is merely illustrative of a computing environment in which the herein described systems and methods may operate, and does not limit the implementation of the herein described systems and methods in computing environments having differing components and configurations. That is to say, the inventive concepts described herein may be implemented in various computing environments using various components and configurations.

Figure 2:
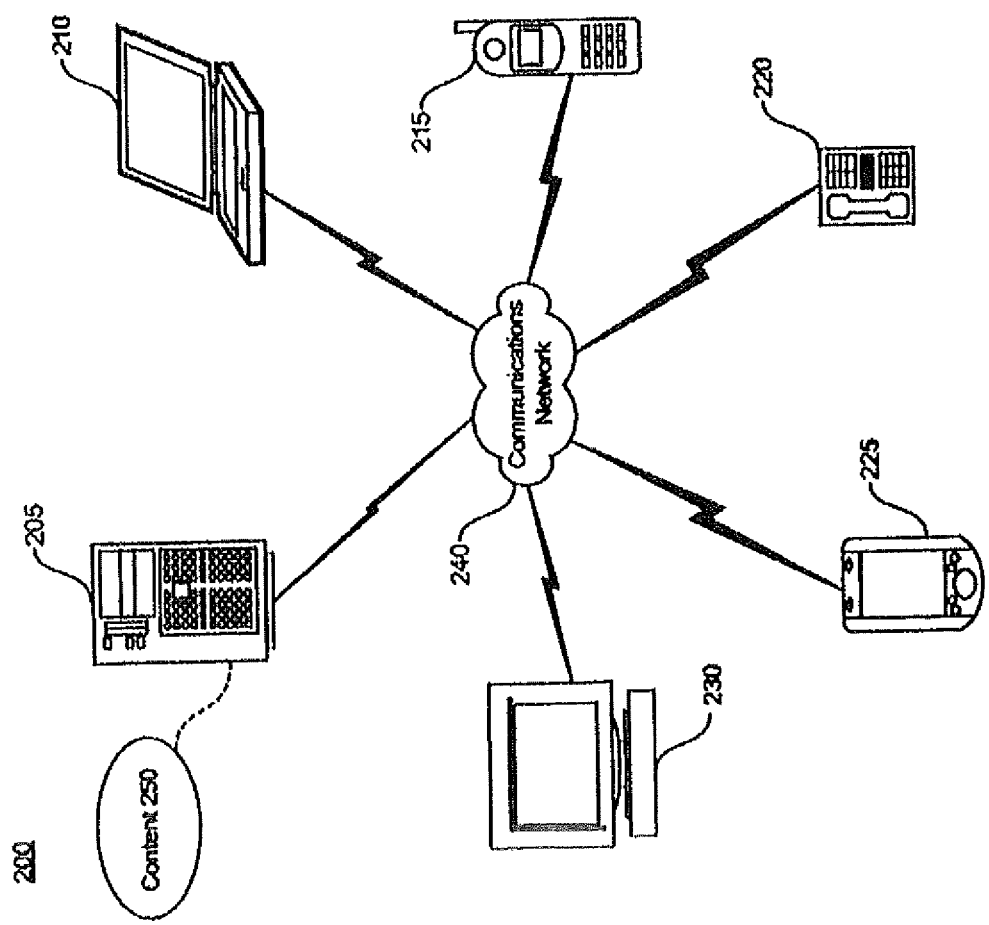
FIG. 2 illustrates a diagram of a system according to embodiments of the present disclosure.

As shown in FIG. 2, computing system 100 may be deployed in networked computing environment 200. In general, the above description for computing system 100 applies to server, client, and peer computers deployed in a networked environment, for example, server 205, laptop computer 210, and desktop computer 230. FIG. 2 illustrates an exemplary illustrative networked computing environment 200, with a server in communication with client computing and/or communicating devices via a communications network, in which the herein described apparatus and methods may be employed.

As shown in FIG. 2, server 205 may be interconnected via a communications network 240 (which may include any of, or any combination of, a fixed-wire or wireless LAN, WAN, intranet, extranet, peer-to-peer network, virtual private network, the Internet, or other communications network such as POTS, ISDN, VoIP, PSTN, etc.) with a number of client computing/communication devices such as laptop computer 210, wireless mobile telephone/smart device 215, wired telephone 220, personal digital assistant 225, user desktop computer 230, and/or other communication enabled devices (not shown). Server 205 may comprise dedicated servers operable to process and communicate data such as digital content 250 to and from client devices 210, 215, 220, 225, 230, etc. using any of a number of known protocols, such as hypertext transfer protocol (HTTP), file transfer protocol (FTP), simple object access protocol (SOAP), wireless application protocol (WAP), or the like. Additionally, networked computing environment 200 may utilize various data security protocols such as secured socket layer (SSL), pretty good privacy (PGP), virtual private network (VPN) security, or the like. Each client device 210, 215, 220, 225, 230, etc. may be equipped with an operating system operable to support one or more computing and/or communication applications, or "apps", such as a web browser (not shown), email (not shown), the dedicated user interfaces and medical device controls discussed herein, or the like, to interact with server 205.

The disclosure provides a genericized and/or normalization medical device architecture that may be particularly useful for maximizing the effectiveness of medical device product design and manufacturing stages of a product development cycle, and that may also be useful for interoperation of, for example, remote interfaces across multiple device types and/or multiple graphical user interfaces (GUIs). Simply put, most medical devices have electromechanical components under software control, and by identifying and employing a software architecture common to these medical devices, the exact capabilities of the electromechanical hardware components may be deferred until later in the development cycle, or may be normalized for use through alternative interfaces and/or GUIs.

Those skilled in the art will appreciate, in light of the disclosed embodiments, that the genericized software architecture may operate on a software module basis. That is, each software module may be, for example, treated as an object in an object-oriented programming environment, and hence each object may have an associated data format. Further, objects having a dedicated purpose will be common across most software and hardware within the same or a related vertical, and hence understanding of a common inclusions and data formats within and across these dedicated objects for software and hardware within the same or a related vertical enables the providing of a software architecture that is at least substantially agnostic, i.e., genericized, across the hardware and software having those same or similar dedicated objects comprising the same or similar data. Accordingly, the present invention may provide a software architecture capable of normalization across software and hardware. As such, the skilled artisan will appreciate that the particular modules discussed throughout are exemplary in nature, and the present invention may perform its genericized functions across the enumerated and other modules known to those skilled in the art.

Due to the software/hardware agnostic nature of the architecture, embodiments of the present disclosure may be applicable to, and interoperable with, many types of devices, and may have particular applicability to medical devices and systems. These medical devices may include, for example, phacoemulsification systems including devices such as a foot pedal, a laser, vitrectomy devices, and the like. Each of these medical devices shares common functionalities and/or needs. For example, each of these medical devices may employ a user interface, which may further have a common look and feel. Each of these devices may also retrieve, handle, and process patient data in a similar manner. Stated another way, these devices may employ similar means to enter, edit, retrieve, store, and share (locally or remotely from diagnostic equipment, for example) patient data, for example through Laboratory information systems and/or Hospital information systems (LIS/HIS). Further, each of these devices must similarly comply with certain standards and policies (e.g., HIPAA).

These commonalities may reflect the fact that these devices (and their correspondent modules, or objects) share similar components genericized to, and interoperable with, any medical device. As such, in a design, a common set of libraries and services in the form of a frame work may be employed to support the production of a genericized medical device. By focusing on the development of a genericized medical device through at least the stages of a development cycle of a medical device, hardware implementation decisions and/or hardware changes can be made at later stages without affecting components that are common to all medical devices. Thus, these deferred product changes may not extend, or further delay, a product's development or time to market.

Figure 3:
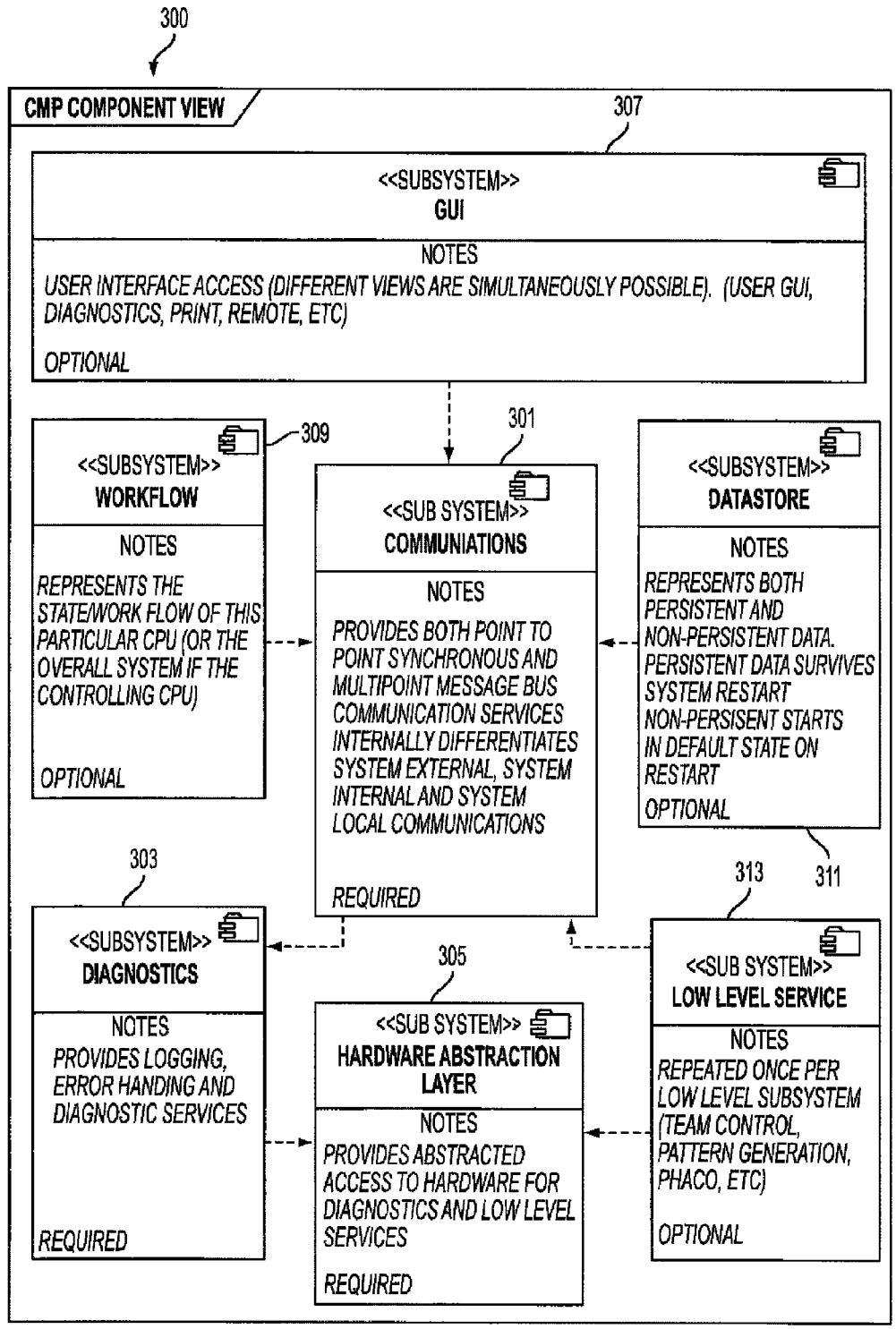
FIG. 3 illustrates an exemplary architecture framework according to embodiments of the present disclosure.

FIG. 3 depicts such a framework in the form of a software architecture 300 having components common to any particular medical device product line. As shown, the software architecture 300 may include a communications subsystem 301, a diagnostics subsystem 303, and a hardware abstraction layer 305. Of note, the discussed modules and layers are exemplary only, and are intended to be illustrative of common modules, subsystems, objects, and the like, employed across different medical devices, such as those within a particular product line. Optionally, the software architecture may include a graphical user interface (GUI) subsystem 307, a workflow subsystem 309, a datastore subsystem 311 (which may be used to store persistent data surviving system restarts and non-persistent data associated with the components), and a low level service subsystem 313.

Embodiments of the present invention may employ the aforementioned communications subsystem to connect each of the software components of the software architecture by providing a communication library to provide a message bus service for implementing point-to-point synchronous and multi-point message bus communication services. The communications subsystem may also serve to internally differentiate among external system, internal system, and local system communications. A further example of the capabilities of the communications subsystem is shown in FIG. 4.

Figure 4:
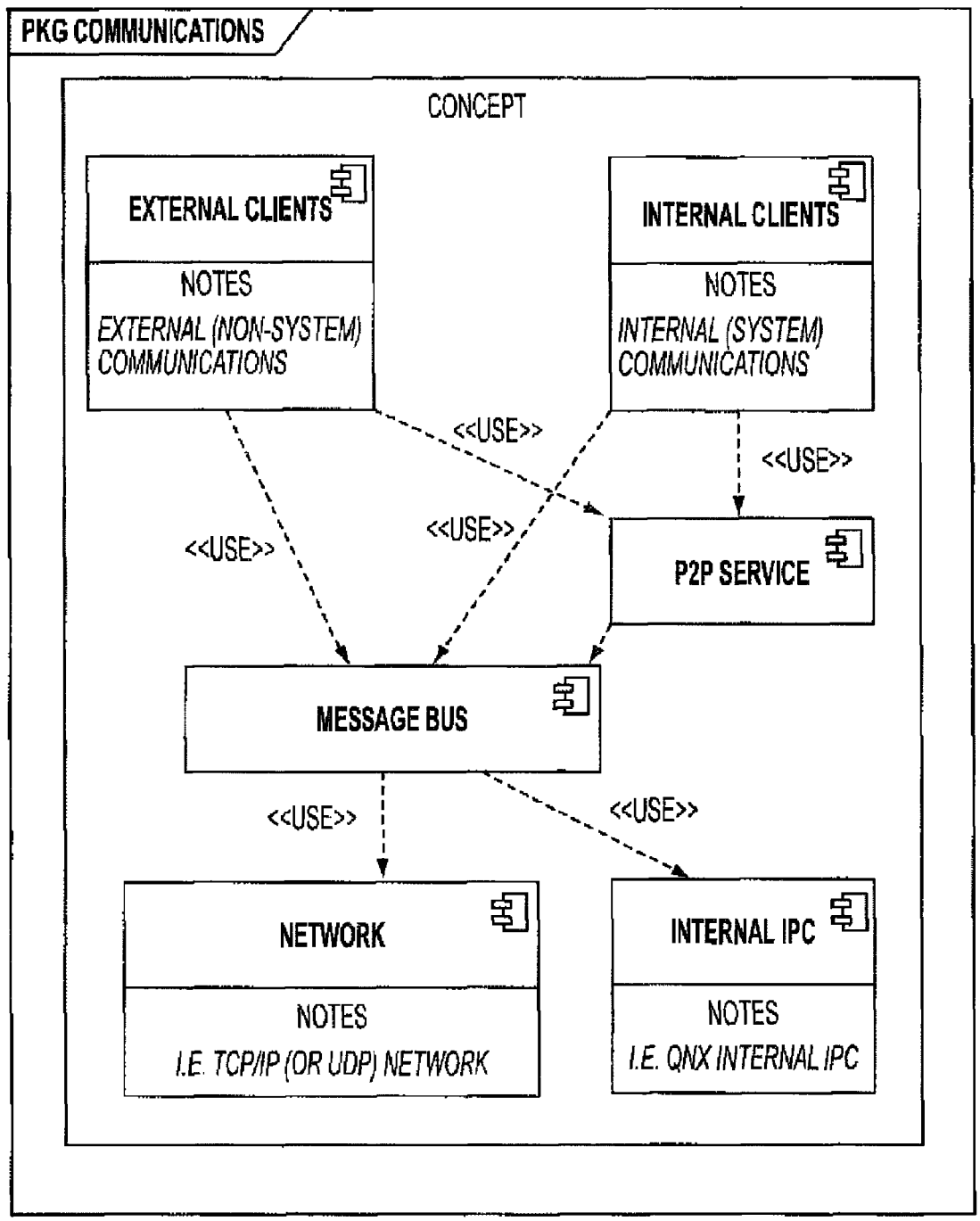
FIG. 4 illustrates an exemplary communications subsystem according to embodiments of the present disclosure.

Referring to FIG. 4, the communications subsystem may provide a message bus service wherein clients may be a source or a sink for messages by using a publish/subscribe metaphor, as known by those in the art. Optional point-to-point services may be provided as needed. The communications subsystem may also be configured to provide optional high priority or high bandwidth attributes. These attributes may imply system design limitations on the software components using them with which to communicate. For easier routing and filtering of messages between and among components, messages may be grouped into "types" and "subtypes".

The communications subsystem may be configured to effectively "hide" the physical location of the endpoint of its communications, resulting in several benefits. For example, this provides looser coupling between components of the software architecture, thus making the system less fragile to hardware and timing changes. Further, it allows the components to be developed separately and potentially in parallel. Parallel, as opposed to serial, production of components may shorten the schedule and, as discussed above, may reduce the impact late breaking product changes may have on the cycle.

Figure 5:
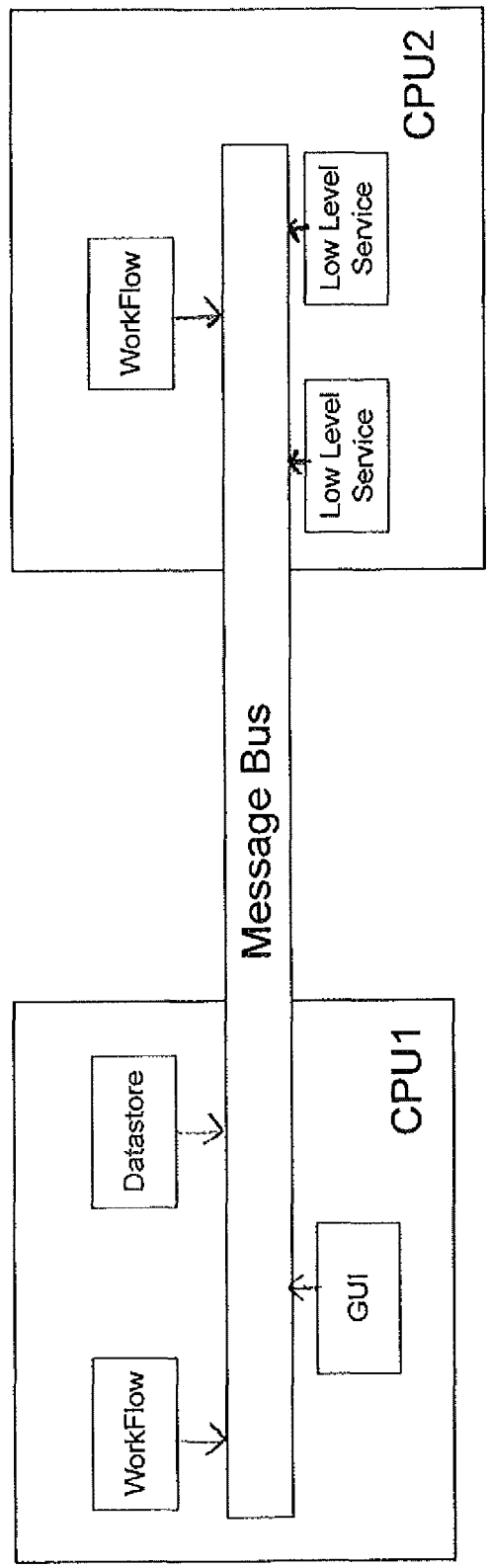
FIG. 5 illustrates a message bus service according to embodiments of the present disclosure.

Accordingly, the afore-discussed communications subsystem may provide a location-independent message bus service that allows the software architecture components to communicate with each other without knowing each other's respective physical location. For example, as shown in FIG. 5, components of a particular device of CPU1 may communicate via the message bus, with components associated with CPU2. Because of the location independent/device agnostic nature of the communications subsystems, it should be appreciated that these components may have no knowledge of the location of one another. As such, at different stages during the development cycle, remote components and/or products may be simulated. More specifically, for example, software components can be tested at the development stage in a software development environment, and no actual equipment is needed, but the testing can be performed fully by software by means of one computer, for example. Terminal emulators have been developed, which totally or partly model the operation of a component. The advantage of application development environments of this kind is that the applications do not have to be loaded in actual devices for observing or testing the functioning of an application of a given medical device. Further, each CPU based device may be independent for service, manufacturing and testing.

In conjunction with the communications subsystem(s), the hardware abstraction layer (HAL) may permit device software to be developed in a hardware independent manner. The HAL may allow for reconfiguration of an existing medical device without the need to modify certain pieces of medical device software. For example, a phacoemulsification system may include medical devices, such as a foot pedal to control, or switch between, different modes of the phaco system based on the level of depression of the pedal. The phaco system may also include an irrigation/aspiration (I/A) handpiece, a vacuum pump, and other medical devices. A vacuum sensor utilized in connection with an I/A handpiece may need to be changed or reconfigured in the course of development of a new phacoemulsification system, for example. However, due to the hardware independent nature of the HAL in conjunction with the software architecture, regardless of changes to the medical device hardware (such as to the aforementioned sensor), any associated medical device software may not be affected.

This level of abstraction provided by the HAL allows for components and devices to be simulated at different stages during the development cycle. More specifically, for example, components can be tested at the development stage in a software development environment, whereby no actual equipment is needed, but the testing can be performed fully by software by means of one computer, for example. For example, operation of a foot pedal and its control of, for example, the I/A handpiece may be tested without the actual physical foot pedal and/or IA handpiece being connected to the system. For example, an emulator, as known in the art and discussed above, may be used, which totally or partly model the operation of the foot pedal and/or IA handpiece.

Figure 6:
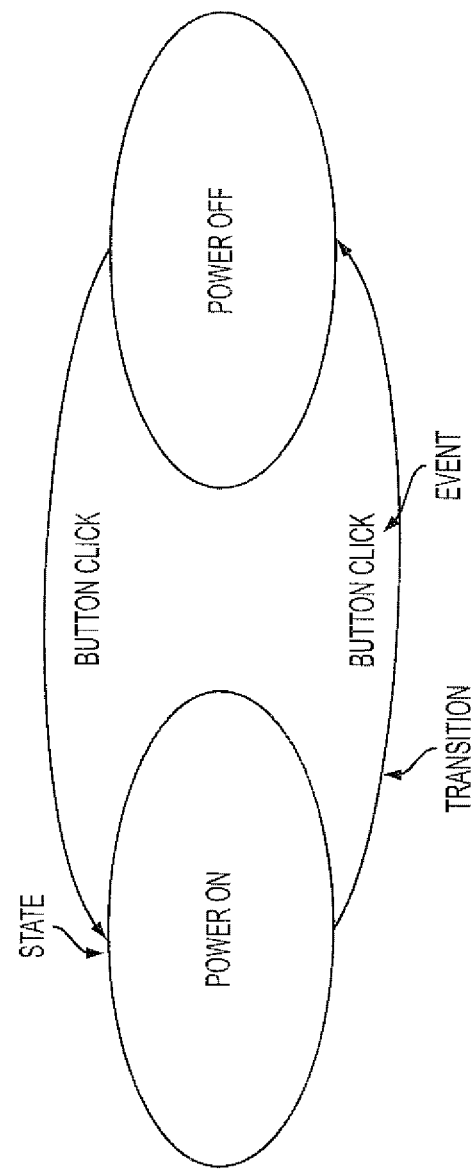
FIG. 6 illustrates a state machine diagram which may be employed in the development of a medical device/system startup.

Much of the behavior and/or operation of components of medical devices, and, in turn, medical devices themselves, may be state-dependent and/or event-driven. As such, a workflow subsystem may be used in the development of software and/or hardware of a medical device. Accordingly, embodiments of the present disclosure may include APIs to allow developers to manage business logic and process flow (i.e., "workflow") of a particular medical device. These APIs may allow a developer to implement a workflow across various subsystems (by, for example, building on the communications subsystem) and support system start up flows, state machines, error handling, patient data entry, and the like. The workflows may represent a sequence of related steps or a device control sequence talking to hardware of a particular medical device. For example, FIG. 6 illustrates a state machine diagram which may be employed in the development of a medical device/system startup. As shown in FIG. 6, a state machine may be implemented with two states: a device "power on" state; and a device "power off" state. The device may be in one of these two states.

These power states may represent any number of medical devices or systems. For example, they may refer to the powering on of a phaco emulsification system, a foot pedal, a targeting system, and the like. The state machine may be designed by the developer to respond to this button depression by either powering on or powering down the particular medical device or system.

A transition moves the state machine into a new state. A transition can only occur in response to an event. For example, when the machine receives a button click event in the "power off" state, it transitions to the "power on" state. Conversely, if the machine is in the "power on" state and receives a button click event, it moves to the "power off" state.

Embodiments of the present disclosure may also include a graphical user interface (GUI) module that provides application program interfaces for the development of means to present information and functionality for users to interact with a medical device. A user can interact with a user interface through a myriad of user interface elements or widgets. The APIs may allow for the development of many different GUI options. For example, the GUI may display information only, such as labels and images, or the GUI may also receive input from a user through an input mechanism, such as menus, buttons and check boxes. Furthermore, these GUI elements may include a graphical element with a collection of input elements. For example, a tree widget may provide a hierarchy of widgets, wherein each widget has its own window, dialog or form for interacting with the medical device. By way of further non-limiting example, display and/or input elements may be placed and arranged within a window, frame, property sheet or other container widget, which may be moved, resized, closed, and the like. Users may interact with user interface elements to view display elements and modify input elements across multiple forms or screens.

As discussed above, embodiments of the present disclosure may also include a diagnostics subsystems which, as the name suggests, may provide diagnostic services to a particular medical device product or system. For example, common to most medical devices, mechanisms may be employed by a product to notify a user to the operational status of a given system of a medical device. More specifically, for example, in conjunction with the GUI subsystem, upon being alerted, a user may, via a screen interface, examine any potential problems with the hardware or associated software of a given medical device. Also, because it uses the afore-discussed hardware abstraction layer, it may not need to know certain implementation specific details of any hardware it may be monitoring.

Embodiments of the present disclosure may also include a low level services subsystem that may provide support to manage single core functionality. This subsystem may allow for the abstraction of a particular hardware feature or for purely computation-based function (e.g., image processing). For example, these low level services may support commands and feedback information that are typically sent and received in terms of the hardware device's physical characteristics. However, by being configured on the communications subsystem, the applications using these low level services are oblivious to the location of the services. Low level services may include support to manage single core functionality, such as phaco system functionality, foot pedal functionality, beam steering, targeting, phaco pump functionality, the aforementioned image processing, and the like.

Figure 7:
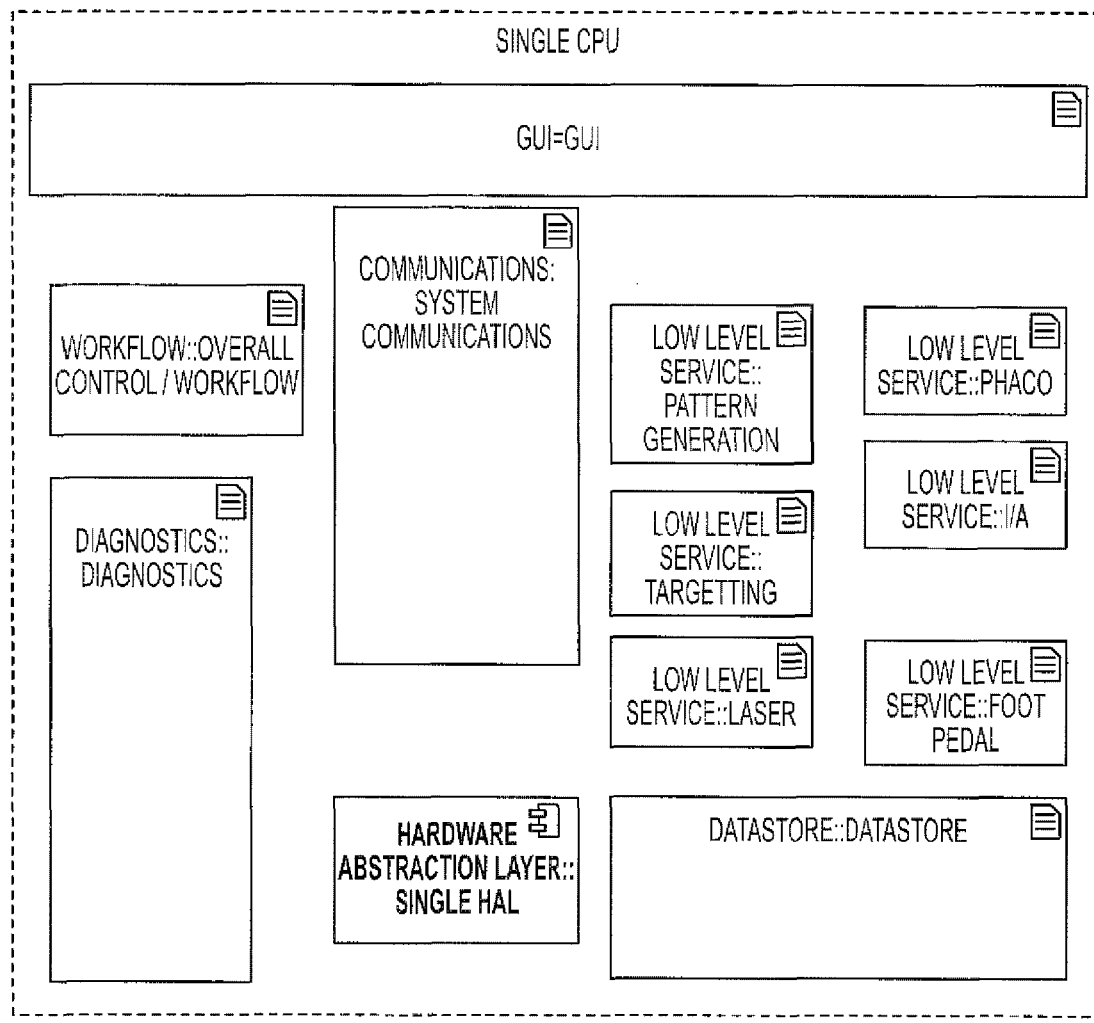
FIGS. 7, 8, and 9 illustrate software architectures according to embodiments of the present disclosure.
Figure 8:
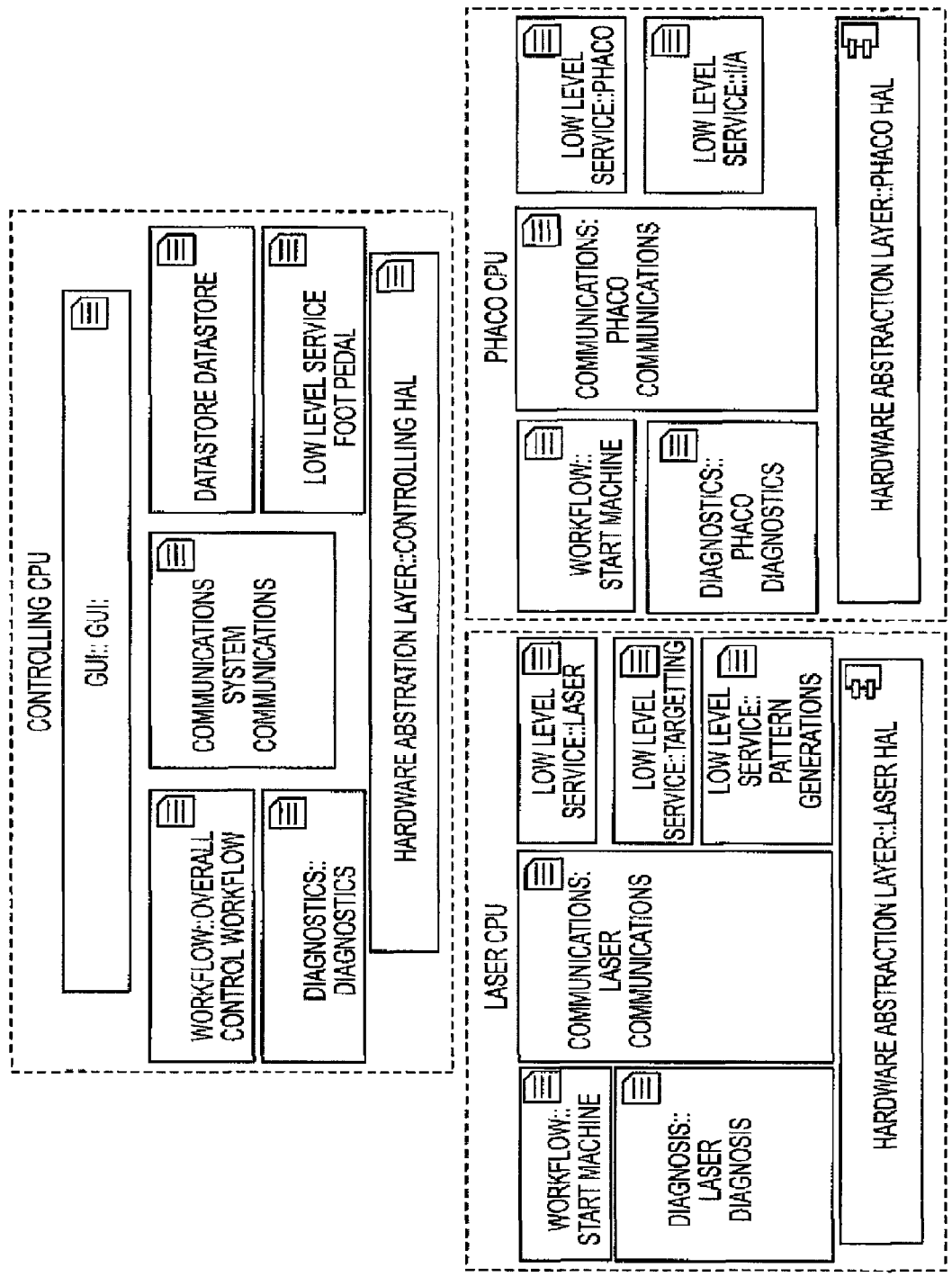
Figure 9:
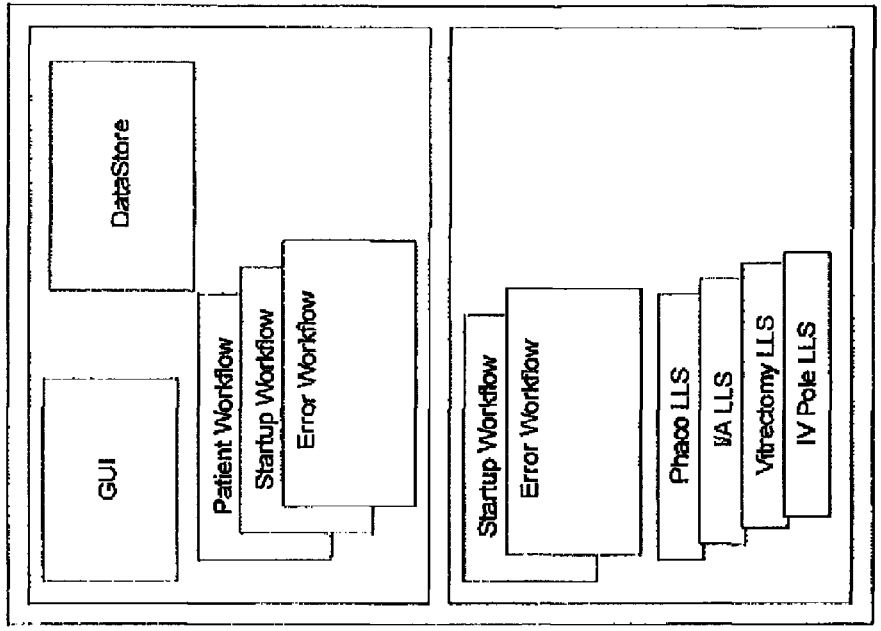
Figure 9:
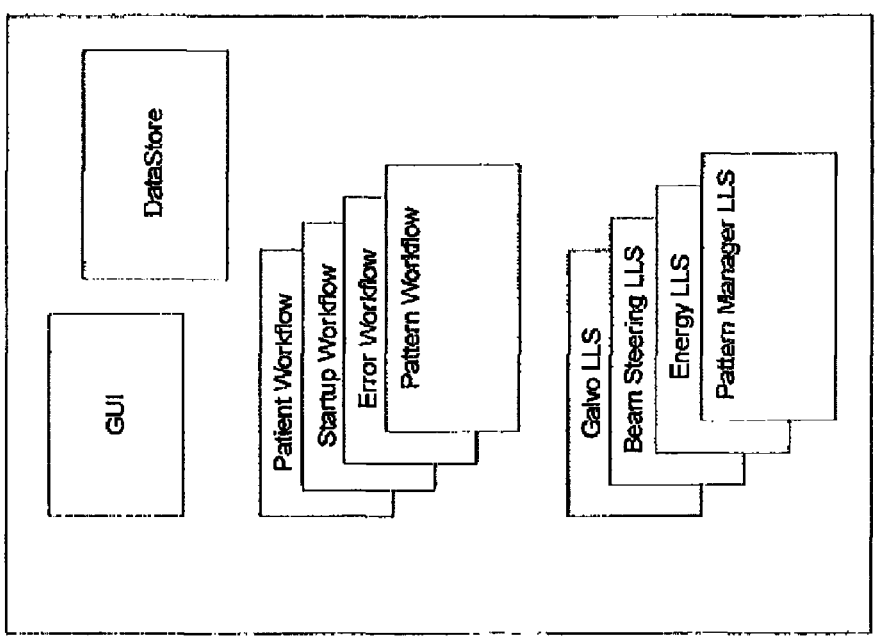

It should be appreciated that the software architecture may be employed in several different configurations. For example, the software architecture may be hosted by computer hardware associated with a single CPU, as shown in FIG. 7, or with multiple CPUs, as illustrated in FIG. 8. As shown in FIG. 8, a controlling CPU 601 may host a software architecture including the afore-discussed components. Accordingly, separate software architectures may be hosted by other CPUs associated with specific medical devices. For example, as shown in FIG. 8, laser CPU may host a software architecture, which includes its own workflow, diagnostic, communications, HAL, and low level service subsystems. A phaco CPU may be similarly situated. However, it should be understood that embodiments of the present disclosure are not so limited, as any number of CPUs and associated computer hardware may be employed in hosting software architectures for the development of any medical device product(s) and/or systems. In another example, as shown in FIG. 9, the software architecture according to embodiments may be employed in existing eye surgery systems, such as the interlase femtosecond laser system (iFS) or WhiteStar Signature systems.

The software architecture 300 may be loaded on a variety of platforms. For example, the illustrated software architecture 300 may be implemented on a broad variety of operating systems, such as Linux, Unix, Microsoft Windows, Apple, MacOS, and the like. A wide variety of computer hardware may also host the software architecture 300 for a medical device or system. For example, the computer hardware may correspond to personal computers, laptop computers, mobile devices, single-board computers, and the like. It will be understood that the computer hardware can be local to the medical device/system or can be remotely located.

Components of the software architecture 300 can be implemented with a variety of different programming languages. By way of non-limiting example only, the components may be implemented with the C++ programming language. The C++ programming language may provide relatively widely standardized support on a variety of platforms with system-level efficiency. In addition, the C++ programming language's support of object oriented technology also promotes a relatively well organized software design.

In accordance with the above, embodiments of the present disclosure may include a computer readable medium having computer-executable instructions for providing the software architecture. The computer readable medium may correspond to a wide variety of mediums including, but not limited to, hard disks, floppy disks, and other magnetic disks, RAM, ROM, flash memory, memory cards, and other solid-state memory, optical disks, CD-ROMs, DVD-ROMs, and the like, as also discussed above with reference to FIGS. 1 and 2.

Figure 10:
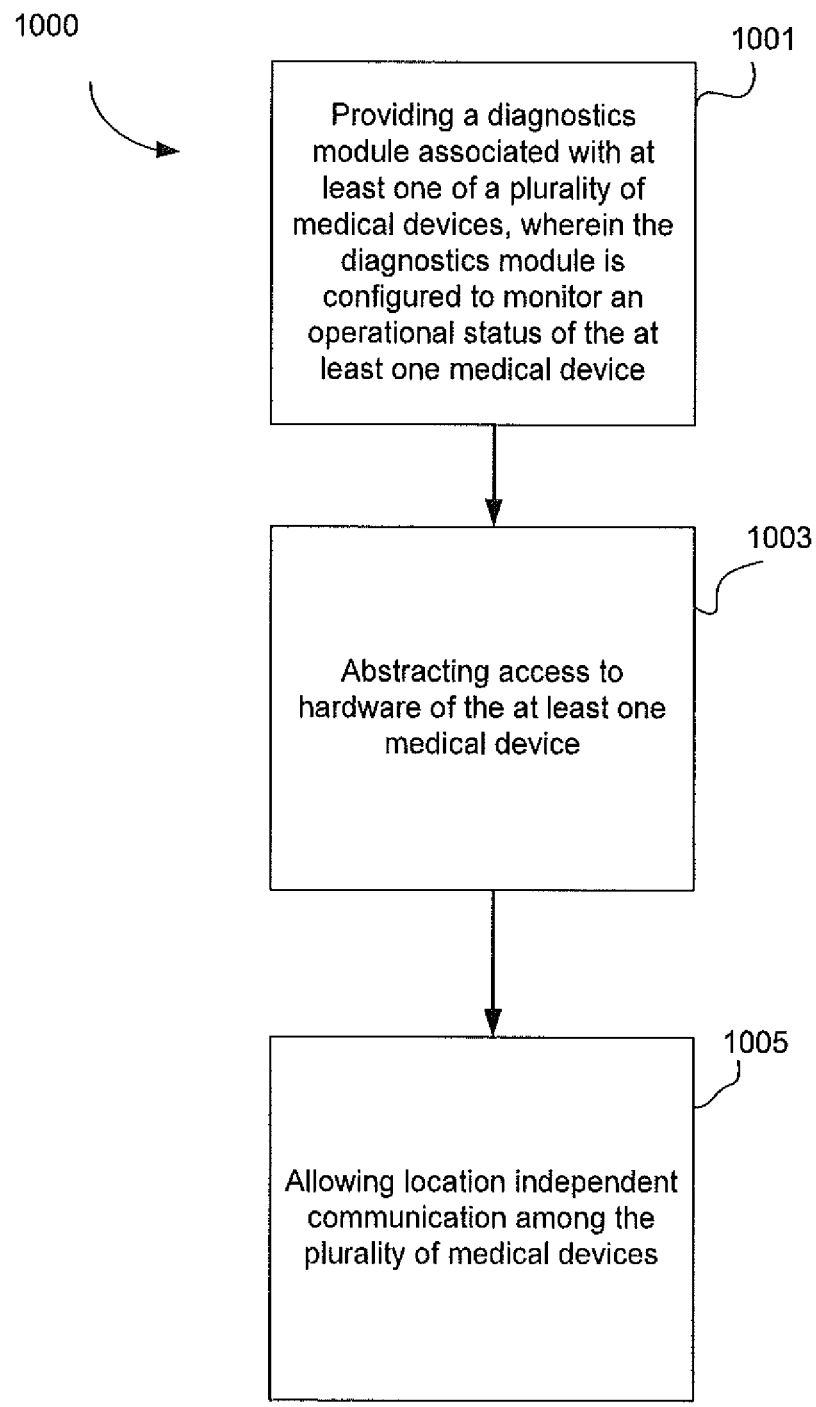
FIG. 10 is a flow diagram illustrating an exemplary method according to the present invention.

In accordance with one or more embodiments described herein, and with reference to FIG. 10, there is shown a methodology 1000 according to embodiments of the present invention. It is noted that numbers associated with the blocks of FIG. 10 do not imply a particular order in which the corresponding steps are to be performed according to the method 1000. In FIG. 10, step 1001 includes providing a diagnostics module associated with at least one of a plurality of medical devices, wherein the at least one diagnostics module is configured to monitor an operational status of the at least one medical device. Step 1003 includes abstracting access to hardware of the at least one medical device. Step 1005 includes allowing location independent communication among the plurality of medical devices.

The previous description of the disclosure is provided to enable any person skilled in the art to make or use the disclosure. Various modifications to the disclosure will be readily apparent to those skilled in the art, and the genericized principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A non-transitory computer readable storage medium having encoded thereon computer executable instructions which, when executed, cause a computer to implement a software architecture common to a plurality of medical devices, the software architecture comprising:
   a plurality of modules each configured to control and monitor aspects of hardware or software related to the plurality of medical devices;
   a location independent communications module configured to provide message bus services for ones of the plurality of modules and hide the physical locations of a plurality of communication endpoints, wherein the ones of the plurality of modules are communicatively associated with each of the plurality of medical devices; and
   a hardware abstraction layer associated with the at least one medical device that is configured to allow hardware independent control of hardware functionality of the at least one medical device, wherein the hardware functionality of the at least one medical device is dependent on physical characteristics of the at least one medical device.

2. The medium of claim 1, wherein one of the plurality of modules is configured to provide at least one application programming interface (API).

3. The medium of claim 1, wherein one of the plurality of modules comprises a diagnostics module associated with the software of at least one of the plurality of medical devices, wherein the diagnostics module is configured to monitor an operational status of the hardware of the at least one medical device.

4. The medium of claim 3, wherein the diagnostics module provides at least one application programming interface (API) to allow for the monitoring of the operational status of the at least one medical device.

5. The medium of claim 1, wherein the hardware abstraction layer provides at least one application programming interface (API) to allow control of the hardware functionality of the at least one medical device.

6. The medium of claim 1, wherein one of the plurality of modules comprises a datastore associated with the at least one medical device, wherein the datastore is configured to provide persistent and non-persistent data storage on the at least one medical device.

7. The medium of claim 1, wherein one of the plurality of modules comprises a graphical user interface (GUI) module capable of communicating using the location independent communications module, and that is configured to allow implementation of graphical views associated with the software of the at least one medical device to a user of the at least one medical device.

8. The medium of claim 7, wherein the GUI module is further configured to provide at least one application programming interface (API) to manage and transition between the graphical views.

9. The medium of claim 1, wherein one of the plurality of modules comprises a low level services library configured to allow implementation of low level services associated with the hardware.

10. The medium of claim 9, wherein the low level services library provides at least one application programming interface (API) to allow for use of the functionality of the at least one medical device.

11. The medium of claim 1, wherein one of the plurality of modules comprises a workflow module configured to allow implementation of a workflow across components of the software architecture.

12. The medium of claim 11, wherein the workflow module provides an application programming interface to support a state machine.

13. The medium of claim 1, further comprising message bus services associated with one or more of the plurality of medical devices, wherein the message bus services comprise data normalization.

14. The medium of claim 13, wherein the data normalization comprises normalization across GUIs.

15. The medium of claim 1, further comprising:
one or more low level service subsystems configured to provide single core functionality to one or more of the plurality of medical devices.

16. The medium of claim 1, wherein the location independent communications module is further configured to:
receive a plurality of messages from the plurality of medical devices,
determine a priority and a type for each of the plurality of messages received,
group the plurality of messages based upon the type to form one or more groupings, and
route the plurality of messages based upon the priority and the one or more groupings.

17. The medium of claim 1, wherein the hardware functionality of the at least one medical device includes beam steering, targeting, or phaco pump functionality.

18. A method of implementing a software architecture common to a plurality of medical devices, comprising:
accessing information from at least one module included in a plurality of modules, wherein each of the plurality of modules is configured to control and monitor aspects of hardware or software related to the plurality of medical devices;
communicatively associating, by a location independent communications module, one or more of the plurality of modules to each of the plurality of medical devices, and hiding physical locations of a plurality of communication endpoints; and
controlling, by a hardware abstract layer, hardware functionality of the at least one medical device, wherein the hardware abstraction layer provides hardware independent control and the hardware functionality of the at least one medical device is dependent on physical characteristics of the at least one medical device.

19. The method of claim 18, further comprising:
providing at least one application programming interface (API) to allow for the providing of a message bus services.

20. The method of claim 18, further comprising:
providing at least one application programming interface (API) to allow for monitoring of an operational status of at least one of the plurality of medical devices.

21. The method of claim 18, further comprising:
providing an application programming interface (API) for managing persistent and non-persistent data associated with at least one medical device.

22. The method of claim 18, further comprising:
implementing graphical views associated with the plurality of medical devices to a user of one of the medical devices using a Graphical User Interface (GUI).

23. The method of claim 22, further comprising, providing application programming interfaces to manage and transition between the graphical views.

24. The method of claim 18, further comprising providing a low level services library configured to allow implementation of low level ones of the hardware.

25. The method of claim 18, further comprising:
implementing a workflow module across one or more of the plurality of medical devices.

26. The method of claim 25, wherein the workflow module provides an application programming interface to support a state machine.

27. The method of claim 18, further comprising:
normalizing data across ones of the plurality of medical devices.

28. The method of claim 27, wherein the data normalization comprises normalization across GUIs.

29. The method of claim 27 further comprising:
receiving, by the location independent communications module, a plurality of messages from the plurality of medical devices,
determining, by the location independent communications module, a priority and a type for each of the plurality of messages received,
grouping, by the location independent communications module, the plurality of messages based upon the type to form one or more groupings, and
routing, by the location independent communications module, the plurality of messages based upon the priority and the one or more groupings.

30. The method of claim 27, wherein the hardware functionality of the at least one medical device includes beam steering, targeting, or phaco pump functionality.

31. The method of claim 18, further comprising:
providing one or more low level service subsystems configured to perform single core functionality to one or more of the plurality of medical devices.

* * * * *